(12) United States Patent
Ryan

(10) Patent No.: US 6,953,469 B2
(45) Date of Patent: Oct. 11, 2005

(54) DEVICE AND METHOD FOR TREATING INTRALUMINAL TISSUE

(75) Inventor: Thomas P. Ryan, Flemington, NJ (US)

(73) Assignee: Ethicon, Inc., Somerville, NJ (US)

(*) Notice: Subject to any disclaimer, the term of this patent is extended or adjusted under 35 U.S.C. 154(b) by 0 days.

(21) Appl. No.: 09/942,412

(22) Filed: Aug. 30, 2001

(65) Prior Publication Data

US 2003/0045869 A1 Mar. 6, 2003

(51) Int. Cl.[7] ............................................. A61M 29/00
(52) U.S. Cl. ..................................... 606/192; 606/27
(58) Field of Search ................................ 606/104, 105, 606/110, 111, 192, 193, 197, 27, 28, 29, 30, 31

(56) References Cited

U.S. PATENT DOCUMENTS

| | | | |
|---|---|---|---|
| 3,875,939 A | | 4/1975 | Bolduc et al. |
| 3,923,051 A | | 12/1975 | Soichet |
| 3,924,628 A | | 12/1975 | Droegemueller et al. |
| 4,182,328 A | | 1/1980 | Bolduc et al. |
| 5,163,949 A | * | 11/1992 | Bonutti .................... 606/192 |
| 5,232,444 A | * | 8/1993 | Just et al. ................ 604/110 |
| 5,443,470 A | * | 8/1995 | Stern et al. .............. 607/98 |
| 5,449,380 A | | 9/1995 | Chin |
| 5,501,681 A | | 3/1996 | Neuwirth et al. |
| 5,549,559 A | * | 8/1996 | Eshel ....................... 604/113 |
| 5,861,021 A | * | 1/1999 | Thome et al. ........... 607/101 |
| 5,868,735 A | | 2/1999 | Lafontaine |
| 5,891,457 A | | 4/1999 | Neuwirth |
| 5,902,251 A | | 5/1999 | vanHooydonk |
| 5,924,714 A | | 7/1999 | Farris et al. |
| 5,947,992 A | * | 9/1999 | Zadini et al. ............ 606/193 |
| 5,954,714 A | * | 9/1999 | Saadat et al. ............ 606/28 |
| 5,964,755 A | | 10/1999 | Edwards |
| 6,026,331 A | | 2/2000 | Feldberg et al. |
| 6,066,132 A | | 5/2000 | Chen et al. |
| 6,066,139 A | | 5/2000 | Ryan et al. |
| 6,077,298 A | * | 6/2000 | Tu et al. .................. 623/1.19 |
| 6,080,129 A | | 6/2000 | Blaisdell |
| 6,216,704 B1 | * | 4/2001 | Ingle et al. .............. 128/898 |
| 6,315,776 B1 | * | 11/2001 | Edwards et al. ........ 606/41 |
| 6,427,089 B1 | * | 7/2002 | Knowlton ................ 607/101 |
| 6,428,536 B2 | * | 8/2002 | Panescu et al. ......... 606/34 |
| 6,470,219 B1 | * | 10/2002 | Edwards et al. ........ 607/101 |

FOREIGN PATENT DOCUMENTS

WO 0054829 9/2000

OTHER PUBLICATIONS

U.S. Ser. No. 09/749,077 entitled "Conformal Surgical Balloon With Varying Wall Expansibility" filed Dec. 27, 2000, Inventors: Kammerer, G.; Dion, D.; Nohilly, M..
U.S. Ser. No. 09/749,180 entitled "Conformal Surgical Balloon", filed Dec. 27, 2002 Inventors: Kammerer, G.; Dion, D.; Nohilly, M.
U.S. Ser. No. 09/961,917 entitled "Device and Method For Aligning With The Tubal Ostium" filed Sep. 24, 2001 Inventor: Ryan, T.

* cited by examiner

Primary Examiner—Kevin T. Truong
Assistant Examiner—Victor X Nguyen

(57) ABSTRACT

A device and method for treating intraluminal tissue employ an inflatable member having a plurality of heating zones adapted for selective activation, whereby one or more of the heating zones can be activated, by one or more energy sources, to deliver heat to selected intraluminal tissue. The inflatable member can be a balloon that is attached to a catheter having a plurality of passageways for delivering fluids (i.e., liquid or air) to internal chambers of the balloon, thereby inflating the balloon. Each energy source is positioned within a corresponding chamber and may be any one of various types, including a piezoelectric cylinder, a microwave antenna, a cylindrical RF (radio-frequency) source, or a resistive heating coil.

22 Claims, 4 Drawing Sheets

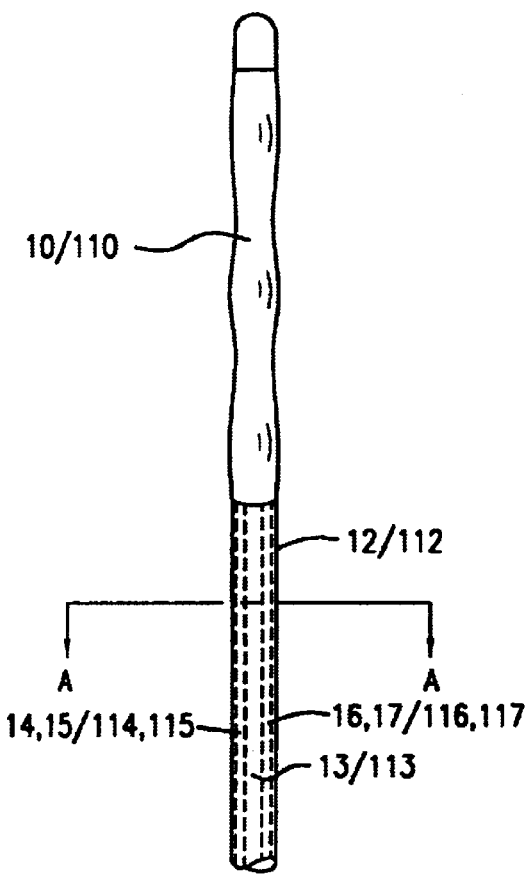
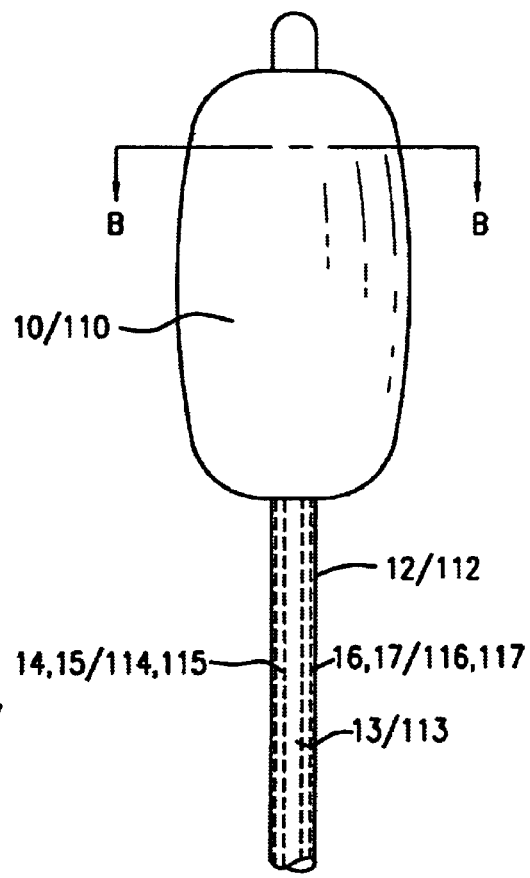
FIG. 1    FIG. 2
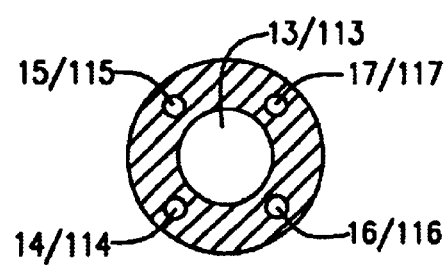
FIG. 1A

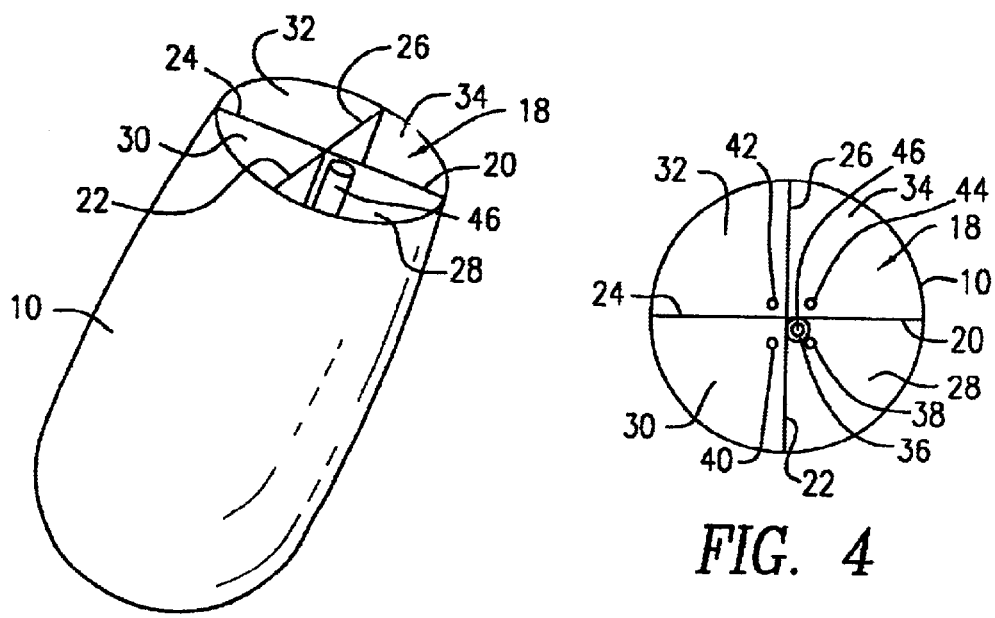
FIG. 3
FIG. 4
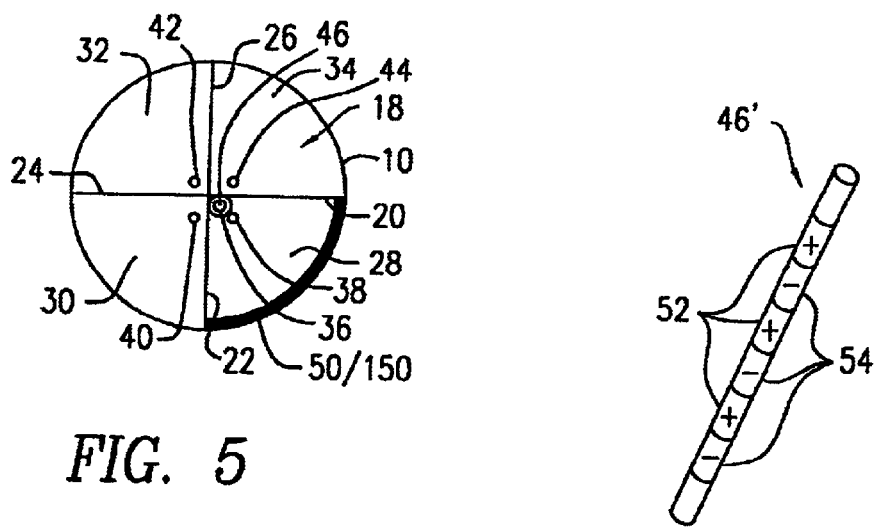
FIG. 5
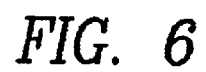
FIG. 6

US 6,953,469 B2

DEVICE AND METHOD FOR TREATING INTRALUMINAL TISSUE

FIELD OF THE INVENTION

The present invention relates to a device and a method for selectively treating intraluminal tissue, especially intraluminal tissue that is diseased.

BACKGROUND OF THE INVENTION

There are a number of surgical procedures that relate to the treatment of intraluminal tissue, i.e., tissue located within a luminal structure such as the esophagus, colon, fallopian tube or urethra. Some of these procedures involve treating intraluminal tissue that is otherwise healthy, while others involve the treatment of diseased intraluminal tissue. For example, during a tubal sterilization procedure on a female patient, the intraluminal mucosal tissue of the fallopian tubes is defunctionalized by heating the tissue, thereby destroying it. In addition, one type of surgical treatment for stress incontinence involves heating the intraluminal tissue of the urethra, thereby shrinking or partially occluding the inner passage of the urethra so as to impede the passage of urine to a small, but necessary, degree. These are only a couple examples of the medical conditions and reasons that involve the controlled treatment of selected intraluminal tissue.

With reference to the treatment of diseased intraluminal tissue, there are various intraluminal disorders that occur in the tissues of luminal structures, including, but not limited to, the esophagus, jejunum, small intestine, fallopian tubes, colon and rectum. Left untreated, such diseases may progress into more serious, and potentially life-threatening, diseases. For example, in Barretts' esophagus the intraluminal mucosal lining has hyperplastic cells that, if left untreated, are at a very high risk over time of developing into malignant tissue, i.e., cancer.

Successful treatment of many such intraluminal disorders can be achieved by the application of heat to the diseased intraluminal tissue from within the luminal structure. However, application of heat radially to the entire circumference of the lumen may result in the unnecessary heating of healthy tissue and, in some cases, also causes stenosis of the luminal structure. Thus, it is preferable for the heat treatment to be applied selectively to the diseased intraluminal tissue or to treat the diseased intraluminal tissue in specified zones spaced over time.

Various methods of treating intraluminal disorders, achieving varying degrees of success, have been developed. For example, coagulation of the mucosal layer of Barretts' esophagus has been attempted using argon beam coagulation. This method of treatment has been less than optimal for the following reasons. First, the argon beam is difficult to initiate when the device is parallel to the esophagus wall. Second, the argon beam requires the surgeon to be relatively close to the esophagus wall. Lastly, the beam quickly quenches and thus leaves a small area of mucosal tissue treated, with untreated zones around it, which results in very spotty, discontiguous treatment of the diseased mucosal tissue.

In addition to the foregoing treatment method, other methods have used surgical ablation tools that require pressure against the mucosa and movement around the target region. Mucousectomy is another treatment method, which involves the surgical removal of the thin mucosal layer of the esophagus. A mucousectomy is difficult to perform because the instrumentation currently available in the GI endoscopy suite does not provide good access to the intraluminal area to be treated.

The device and method of the present invention address the shortcomings of the foregoing treatments for intraluminal tissues by providing for the selective heat treatment of a selected contiguous area of intraluminal tissue.

SUMMARY OF THE INVENTION

The present invention relates to a device for treating intraluminal tissue and includes an inflatable member having a plurality of heating zones and activating means for selectively activating the heating zones, whereby one or more of the heating zones can be activated to deliver heat to selected intraluminal tissue. In one embodiment, the inflatable member is a balloon that is attached to a catheter. The catheter has a plurality of passageways for delivering fluids (i.e., liquid or air) to internal chambers of the balloon, each chamber defining a corresponding heating zone. The activating means includes at least one energy source, each energy source being positioned within a corresponding chamber of the balloon. The energy source may be any one of various types, including a piezoelectric cylinder, a microwave antenna, a cylindrical RF (radio-frequency) source, or a resistive heating coil. The type of fluids that are selected to fill the chambers, and thereby inflate the balloon, depend upon the type of energy source that is used.

In use, the inflatable member is inserted into the luminal structure of a patient. After the inflatable member is inflated in situ, its heating zones are selectively activated, thereby delivering heat to selected intraluminal tissue.

BRIEF DESCRIPTION OF THE DRAWINGS

For a better understanding of the present invention, reference is made to the following detailed description of various exemplary embodiments considered in conjunction with the accompanying drawings, in which:

FIG. 1 is a schematic front elevational view of the device of the present invention, having an inflatable balloon that is connected to a catheter, the balloon being shown in its deflated condition;

FIG. 1A is a cross-sectional view of the catheter of the device of FIG. 1, taken along section line A—A and looking in the direction of the arrows, showing the longitudinal passageways therethrough;

FIG. 2 is a schematic front elevational view of the device shown in FIG. 1, with the balloon in its inflated condition;

FIG. 3 is a schematic perspective cross-sectional view of a first exemplary embodiment of the balloon shown in FIG. 2, taken along section line B—B and looking in the direction of the arrows, showing the inner chambers of the balloon and an energy source inserted into an activated chamber;

FIG. 4 is a schematic top view of the balloon shown in FIG. 3;

FIG. 5 is a schematic top view of the balloon shown in FIG. 3, wherein the energy source is an active RF source electrode and the activated chamber has a return electrode therein;

FIG. 6 is a schematic view of an alternative type of RF source having alternating active and return electrodes;

DETAILED DESCRIPTION OF THE INVENTION

Figure 7:
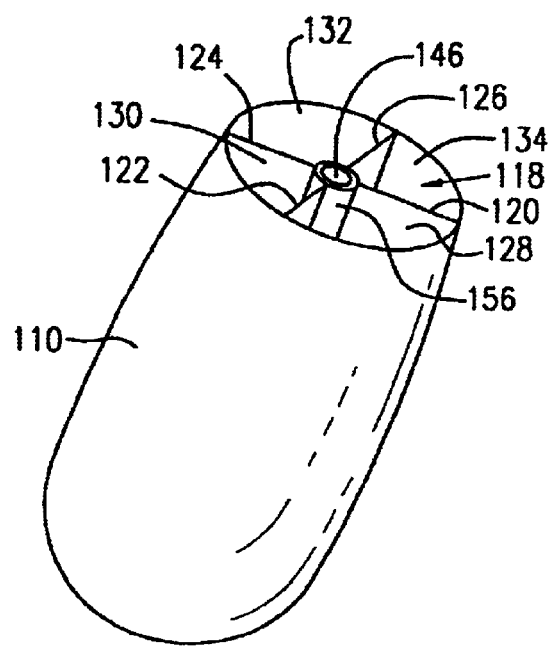
FIG. 7 is a schematic perspective cross-sectional view, similar to FIG. 3, of a second exemplary embodiment of the balloon of the present invention, showing the inner chambers of the balloon and a central axial lumen with an energy source inserted therethrough.

With reference to FIGS. 1, 1A and 2, the device of the present invention includes an inflatable member, or balloon 10, which is connected proximately to the end of a flexible or semi-rigid tube-like structure, such as a catheter 12. The catheter 12 is a conventional type of medical catheter, well known in the art. As will be described in further detail hereinafter, the catheter 12 is used to deliver fluid to the inflatable balloon 10 and has a plurality of passageways 13, 14, 15, 16, 17 for this purpose. More particularly, as can be seen most clearly in FIG. 1A, the catheter has a central longitudinal passageway 13 and plurality of intramural longitudinal passageways, 14, 15, 16, 17. The dimensions of the catheter 12 depend upon the luminal structure that the catheter will be used to treat and are determined in accordance with the typical dimensions for medical catheters.

Referring still to FIGS. 1 and 2, the balloon 10 is made of a relatively flexible biocompatible material such as latex, polyurethane, or silicone. The balloon 10 is approximately 5 centimeters to 10 centimeters in length, depending upon the longitudinal extent of the intraluminal tissue to be treated within the luminal structure. As shown in FIG. 1, prior to insertion into the luminal structure (not shown), the balloon 10 is in its deflated condition and has a diameter that is substantially the same as the catheter 12.

As shown FIG. 2, after insertion into the luminal structure (not shown), the balloon 10 inflates to a cylindrical shape having a diameter of between approximately 2 millimeters and 20 millimeters, depending upon the inner diameter of the luminal structure into which the balloon will be inserted. More particularly, the diameter of the balloon 10 in its inflated condition should be large enough to cause slight dilation of the luminal structure. This ensures firm and continuous contact between the outer wall of the inflated balloon 10 and the selected intraluminal tissue of the inner wall of the luminal structure that is to be treated with heat from the balloon 10, as discussed hereinafter.

Referring now to FIGS. 3 and 4, a first exemplary embodiment of the balloon 10 of the present invention is shown in its inflated condition and without the catheter 12. As seen in FIGS. 3 and 4, the balloon 10 includes an inner cavity 18 having four baffles 20, 22, 24, 26, which divide the inner cavity 18 into four axial chambers 28, 30, 32, 34. As also can be seen in FIGS. 3 and 4, at the bottom of the balloon 10, proximate to the catheter 12, there is a plurality of die cut holes 36, 38, 40, 42, 44, which provide openings into the chambers 28, 30, 32, 34, for a purpose to be described hereinafter. More particularly, two of the holes 36, 38 open into the chamber 28, and each of the remaining holes 40, 42, 44 open into a corresponding one of the remaining chambers 30, 32, 34, respectively.

The balloon 10 is connected to the catheter 12, in a known manner, such that the longitudinal passageways 13, 14, 15, 16, 17 of the catheter 12 communicate, through the holes 36, 38, 40, 42, 44, with the chambers 28, 30, 32, 34 of the balloon 10. More particularly, the central longitudinal passageway 13 of the catheter 12 aligns with the hole 36 such that the central longitudinal passageway 13 communicates with one of the chambers 28 of the balloon 10, for a purpose that will be clarified hereinafter. One or more of the intramural longitudinal passageways 14, 15, 16, 17 of the catheter 12 align with corresponding holes 38, 40, 42, 44 such that one, or more, of the intramural longitudinal passageways 14, 15, 16, 17 communicates with a corresponding one, or more, of the chambers 28, 30, 32, 34 of the balloon, for a purpose that will be clarified hereinafter.

The balloon 10 further includes an energy source 46 that is inserted into the chamber 28, which is referred to hereinafter as the activated chamber. More particularly, the energy source 46 is inserted into the central longitudinal passageway 13 of the catheter 12, through the hole 36 of the balloon, and into the activated chamber 28. The energy source 46 may be any one of various types, including a piezoelectric cylinder (ultrasound source), a microwave antenna, an RF (radio-frequency) source, or a resistive heating coil. It is noted that, while it is possible to use other types of energy sources, the following discussion of the first exemplary embodiment of the present invention will discuss, in particular, the use of the four types of energy sources listed above.

In general, the balloon 10 of the present invention achieves the object of applying heat to selected intraluminal tissue by controlling the directionality of the heat transfer through the chambers 28, 30, 32, 34 of the balloon 10. More particularly, by filling the activated chamber 28 with an appropriate fluid and filling the remaining chambers 30, 32, 34 with a different fluid (i.e., liquid or air), the vast majority of the heat created by the energy source 46 passes through the activated chamber 28 of the balloon 10 to the targeted intraluminal tissue, while the remaining chambers 30, 32, 34 transmit significantly less heat, or no heat at all, to the remaining intraluminal tissue. It is noted that the chambers are filled with the aforesaid fluids, by known conventional methods, through one or more of the intramural longitudinal passageways 14, 15, 16, 17 of the catheter 12 and through the holes 38, 40, 42, 44 aligned therewith, which, as stated previously above, communicate with one, or more, of the chambers 28, 30, 32, 34 of the balloon 10. In addition, where desired, the aforesaid fluids can be circulated into and out of the chambers 28, 30, 32, 34 through the intramural longitudinal passageways 14, 15, 16, 17 of the catheter 12, by known and conventional methods. The fluids that are used to fill or circulate through the chambers 28, 30, 32, 34 depend upon the type of energy source 46 that is used, as follows.

Where the energy source 46 is a piezoelectric cylinder, which emits acoustic ultrasound energy, the activated chamber 28 is filled with water, saline solution or gel, which will transmit the acoustic energy. The remaining three chambers 30, 32, 34 are filled with air, which will not absorb or transmit the acoustic energy emitted by the piezoelectric cylinder. Thus, in the foregoing configuration, the ultrasound energy transmitted by the piezoelectric cylinder energy source 46 would be transmitted through only the activated chamber 28 to the selected intraluminal tissue adjacent to the activated chamber 28. The air in the remaining three chambers 30, 32, 34 would insulate the remaining intraluminal tissue adjacent to these chambers 30, 32, 34 from the acoustic energy.

Alternatively, where the energy source 46 is a microwave antenna, which emits microwave energy, the activated chamber 28 is filled with deionized water or air, which is ideal for transmitting microwave energy to the selected intraluminal tissue adjacent thereto. Saline solution, which absorbs the electromagnetic field created by the emitted microwave energy, is circulated into and out of the remaining three chambers 30, 32, 34 of the balloon 10 to remove the heat therefrom, thereby cooling the remaining intraluminal tissue adjacent thereto. Alternatively, all four chambers 28, 30, 32, 34 can be filled with saline solution, but the saline solution circulated through only the remaining three chambers 30, 32, 34. By not circulating the saline solution through the activated chamber 28, the saline solution will absorb and be heated by the microwave energy and then transmit the heat energy to the adjacent intraluminal tissue selected for treatment.

Where a resistive heating coil is used as the energy source 46, the activated chamber 28 of the balloon 10 is filled with non-circulating water, which is heated by the resistive heating coil and, in turn, transmits heat to the selected intraluminal tissue that is adjacent to the activated chamber 28. The water could be circulated to eliminate thermal gradients but kept inside the activated chambers 28. The remaining three chambers 30, 32, 34 are filled with circulating water, which may absorb some of the heat from the adjacent heated active chamber 28 but, since it is being circulated, will transport the absorbed heat out of the balloon 10, thereby keeping the three remaining chambers 30, 32, 34 and the adjacent intraluminal tissue cool. Alternatively, the three remaining chambers 30, 32, 34 may be filled with air, either circulating or not, to provide insulation from the heat generated by the resistive heating coil energy source 46 in the activated chamber 28.

With reference to FIG. 5, where the energy source 46 is an RF (radio frequency) source, it includes an active RF source electrode 48. A return electrode 50 is provided by coating the interior wall of the active chamber with a conductive metal or polymer. It is noted that the frequency emitted by the active RF electrode is preferably in the range of approximately 200–700 kHz.

In addition, when an RF source is used as the energy source 46, the activated chamber 28 is filled with saline solution. In the configuration described above, i.e., having an active RF source electrode 48 and a return electrode 50, the saline solution absorbs the RF energy and is heated and then, in turn, heats the selected intraluminal tissue. To optimize the homogeneous distribution of heat in the saline solution, the saline solution can be circulated in the activated chamber 28, thereby increasing the convective transfer of heat within the active chamber 28. The remaining three chambers 30, 32, 34 are filled with air, which will not absorb or transmit the RF energy, thereby insulating the remaining intraluminal tissue that is adjacent to the remaining three chambers 30, 32, 34.

It is noted that alternative configurations are possible using an RF source as the energy source 46. As shown in FIG. 6, for example, an RF source 46' that includes two or more alternating active and return electrodes 52, 54 (designated by a "+" sign and a "−" sign, respectively) could be used, thereby eliminating the necessity of having a return electrode 50 coated onto the inner wall of the active chamber 28. The alternating active and return electrodes 52, 54 can be either adjacent (as shown in FIG. 6) or spaced from one another. It is, again, recommended that the saline solution can be circulated in the activated chamber 28 to optimize the homogeneous distribution of heat throughout the saline solution in the activated chamber 28. Furthermore, if the frequency of the active RF source electrode 48 of the former configuration is increased to approximately 2–12 MHz, and a return electrode is placed somewhere on the patient. The RF source will capacitatively couple to the patient through the saline solution-filled activated chamber 28. An alternate device would permanently affix an energy source in every chamber so that no insertion or removal would be required. In this alternate device, the energy sources are part of the assembly and would be disposed of after treatment use.

A second preferred embodiment, shown in FIGS. 7 and 8, will now be described in detail. It is noted that, elements illustrated in FIGS. 7 and 8, which correspond to the elements described above with respect to FIGS. 3 and 4, have been designated by corresponding reference numerals increased by one hundred. The second embodiment of FIGS. 7 and 8, as well as the various elements thereof, are constructed and designated for use in the same manner as the embodiment of FIGS. 3 and 4 and the elements thereof, unless otherwise stated.

Figure 8:
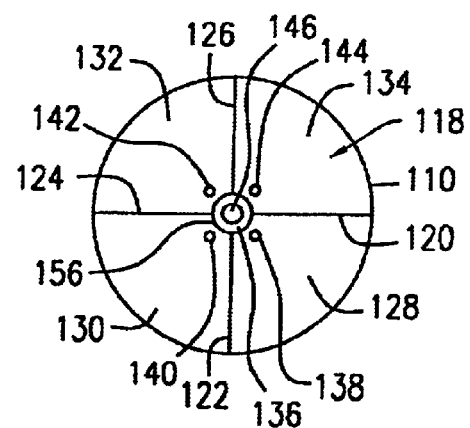
FIG. 8 is a schematic top view of the second embodiment of the balloon shown in FIG. 7.
Figure 9:
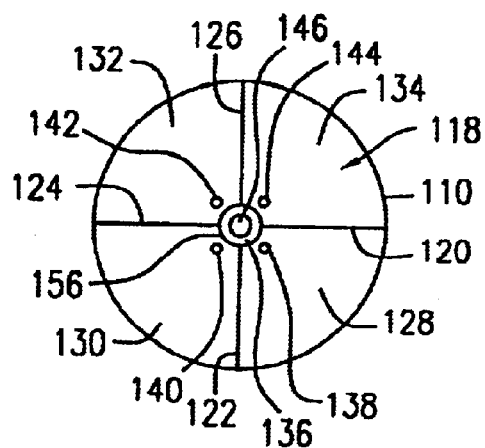
FIG. 9 is a schematic top view of the balloon shown in FIG. 7, wherein the energy source is an active RF source electrode and the activated chamber has a return electrode therein.

With reference now to FIGS. 7 and 8, a second exemplary embodiment of the balloon 110 of the present invention is shown, in its inflated condition and without the catheter 112 (see FIGS. 1 and 2). As seen in FIGS. 7 and 8, the balloon 110 includes an inner cavity 118 having a central axial lumen 136 and four baffles 120, 122, 124, 126 therein. As in the first exemplary embodiment, the baffles 120, 122, 124, 126 divide the inner cavity 118 into four axial chambers 128, 130, 132, 134. The chambers 128, 130, 132, 134 are positioned circumferentially about the axial lumen 136. Furthermore, the balloon 110 is provided with a plurality of holes 138, 140, 142, and 144, that are proximate to the catheter 112 and communicate with chambers 128, 130, 132, and 134.

With reference still to FIGS. 7 and 8, it is noted that, like the embodiment described above in connection with FIGS. 3 and 4, the balloon 110 and the catheter 112 are connected in a conventional and known manner. In the second exemplary embodiment, however, the central longitudinal passageway 113 of the catheter 112 communicates with the central axial lumen 156 of the balloon 110 via the hole 136 of the balloon 110. One or more of the intramural longitudinal passageways 114, 115, 116, 117 of the catheter 112 align with corresponding holes 138, 140, 142, 144 such that one, or more, of the intramural longitudinal passageways 114, 115, 116, 117 communicates with a corresponding one, or more, of the chambers 128, 130, 132, 134 of the balloon 110.

The balloon 110 of the second exemplary embodiment further includes an energy source 146 that is inserted through the central longitudinal passageway 113 of the catheter 112 and into the axial lumen 156 of the balloon 110. The energy source 146 may be any one of various types, including a piezoelectric cylinder, a microwave antenna, a cylindrical RF (radio-frequency) source, or a resistive heating coil. It is noted that, while it is possible to use other types of energy sources, the following will discuss, in particular, the use of the four types of energy sources listed above. Moreover, in the second exemplary embodiment, the energy source 146 is preferably a piezoelectric cylinder or a microwave antenna.

In the second exemplary embodiment of the present invention, the chambers 128, 130, 132, 134 of the balloon 110 are filled with different types of fluids which are selected, depending upon the type of energy source 146 that is inserted into the axial lumen 156, in the same manner as discussed above in connection with the first exemplary embodiment. It is further noted that the activated chamber of the second embodiment is the chamber 128, which transmits the energy emitted by the energy source 146 by virtue of the fluid with which it is filled. For example, where the energy source 146 is a piezoelectric cylinder, the activated chamber 128 is filled with water, saline solution or gel, which will transmit the acoustic energy, while the remaining three chambers 130, 132, 134 are filled with air, which will not absorb or transmit the acoustic energy emitted by the piezoelectric cylinder. Thus, in the foregoing configuration, the activated chamber 128 transmits the ultrasound energy to the selected intraluminal tissue adjacent thereto. The energy source as depicted in FIG. 10A, could also be rotated to affect the tissue in contact with the chamber made active by the rotation.

It should be noted that where the energy source 146 is an RF source, the axial lumen 156 must have a plurality of holes (not shown) that communicate only with the activated chamber 128 so as to allow the fluid in the activated chamber 128 to physically contact the energy source 146. This is because the energy transmitted by an RF source must be in direct contact with the medium (i.e., fluid), which is to absorb the emitted energy and transmit it as heat. Additionally, there must be a return electrode 150 provided in the activated chamber 128, for example, as shown in FIG. 5, a coating of conductive metal or polymer material on the inside wall of the activated chamber 128. Alternatively, the RF source 46' described above and shown in FIG. 6, which has alternating active and return electrodes 52, 54, could be inserted into the axial lumen 156 of the second exemplary embodiment, thereby eliminating the necessity of having a separate return electrode 150 within the activated chamber 128.

Figure 10A:
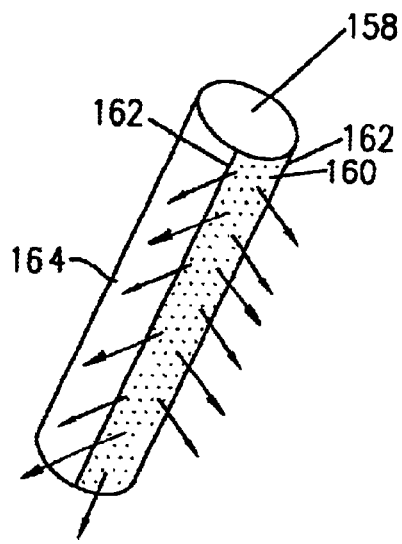
FIG. 10A is a schematic perspective view of a channeled piezoelectric cylinder to be used in connection with the embodiment of FIGS. 7 and 8.
Figure 10B:
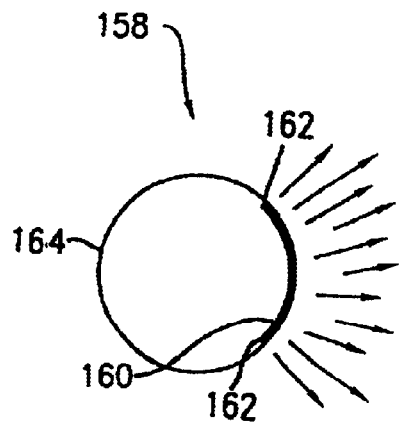
FIG. 10B is a schematic top plan view of the channeled piezoelectric cylinder of FIG. 10A.

In a third exemplary embodiment, which is constructed similarly to the second embodiment of FIGS. 7 and 8, the energy source 146 may be a channeled piezoelectric cylinder 158 having channels 162 therein, which are shown schematically in FIGS. 10A and 10B. The channels 162 are cut axially on the outside surface 164 of the piezoelectric cylinder 158. The activated section 160 of the channeled piezoelectric cylinder 158 transmits the acoustic ultrasound energy in only a limited pre-selected radial direction, shown by the arrows in FIGS. 10A and 10B, which is defined by the location of the channels 162. Such a channeled piezoelectric cylinder 158 can be inserted into the axial lumen 156 of the balloon 110 shown in FIGS. 7 and 8 such that the ultrasound energy is transmitted in the direction of the activated chamber 128. Alternatively, the axial lumen 156 could be entirely replaced by the channeled piezoelectric cylinder 158.

With reference to each of the exemplary embodiments discussed above, it is contemplated that more than one of the chambers 28, 30, 32, 34, 128, 130, 132, 134 of the balloon 10, 110 could be made into activated chambers by filling them with, or circulating therethrough, the appropriate fluid, as specified above. In this way, the heat treatment could be applied to a wider radial area, in the event that the area of the selected intraluminal tissue required a wider zone of treatment. In addition, it is noted that the balloon 10, 110 may have more or less than four chambers 28, 30, 32, 34, 128, 130, 132, 134, as is described above in connection with the exemplary embodiments. For example, the balloon 10, 110 could be provided with only two or three chambers, or up to eight chambers. Furthermore, the balloon 10, 100 could have an additional set of chambers positioned adjacent to the first set of chambers 28, 30, 32, 34, 128, 130, 132, 134, i.e., longitudinally on either side of the first set of chambers 28, 30, 32, 34, 128, 130, 132, 134.

With reference now to the method of the present invention, the balloon 10, 110 and the catheter 12, 112 of the present invention are inserted, with the balloon 10, 110 in its deflated condition as shown in FIG. 1, into a luminal structure having intraluminal tissue to be treated. More particularly, the balloon 10, 110 is inserted into the luminal structure such that the activated chamber 28, 128 is proximate and adjacent to the selected intraluminal tissue to be treated. The balloon 10, 110 is then inflated by filling the chambers 28, 30, 32, 34, 128, 130, 132, 134 with the appropriate fluids, depending upon the type of energy source 46, 146 being used, as discussed above, and circulating the fluids in and out of the chambers 28, 30, 32, 34, 128, 130, 132, 134, as necessary. The aforesaid inflation of the balloon 10, 110 will slightly dilate the luminal structure, thereby ensuring that good, continuous contact is achieved between the balloon 10, 110 and the intraluminal tissues. The energy source 46, 146 is then activated to emit its corresponding type of energy. The energy source 46, 146 is activated for the period of time that is required to achieve penetration of the heat into the selected intraluminal tissue to a depth of approximately 2 millimeters to 3 millimeters, or as deep as otherwise required. It is noted that a resistive heating coil or an RF source will require more time to achieve the same depth of tissue penetration as a piezoelectric cylinder or a microwave antenna. It is contemplated that the patient will undergo up to three additional such treatments, spaced over time.

It will be understood that the embodiments described herein are merely exemplary and that a person skilled in the art may make many variations and modifications without departing from the spirit and scope of the present invention. For instance, one or more temperature probes can be provided within the activated chamber 28, 128 to monitor the temperature achieved. In addition, one or more temperature probes can be provided on the exterior of the balloon 10, 110, proximate to the activated chamber 28, 128, to monitor the temperature of the treatment that is actually delivered to the selected intraluminal tissue. Furthermore, the operation of the balloon 10, 110 can be automated, in a known and conventional manner, by using a computer system and appropriate software, to assist in the placement of the balloon 10, 110 within the luminal structure or to monitor and control the temperature of the chambers 28, 30, 32, 34, 128, 130, 132, 134 and the circulation rates of the fluids in the chambers 28, 30, 32, 34, 128, 130, 132, 134. All such variations and modifications are intended to be included within the scope of the invention as defined in the appended claims.

I claim:

1. A device for treating intraluminal tissue, comprising an inflatable member having an interior which is divided into a plurality of internal chambers arranged in a circular array, each of said chambers defining a heating zone; and activating means for selectively activating one or more of said heating zones deliver heat to intraluminal tissue over a selected radially extending area, said activating means including at least one energy source positioned within said interior of said inflatable member, said at least one energy source cooperating with said heating zones to directionally heat the intraluminal tissue.

2. A device according to claim 1, wherein each of said chambers is adapted to receive a fluid therein.

3. A device according to claim 2, wherein said at least one energy source is located within a corresponding one of said chambers.

4. A device a cording to claim 3 further comprising en insertion member including delivering means for delivering fluid to said chambers.

5. A device according to claim 4, wherein said delivering means includes a plurality of passageway, each of said passageways communicating with a corresponding one of said chambers.

6. A device according to claim 5, wherein a first fluid is supplied to any of said chambers which contains said at least one energy source; and wherein a second fluid is supplied to any of said chambers which does not contain said at least one energy source.

7. A device according to claim 6, wherein said at least one energy source includes a piezoelectric element.

8. A device according to claim 7, wherein said first fluid is water and said second fluid is air.

9. A device according to claim 7, wherein said first fluid is a saline solution and said second fluid is air.

10. A device according to claim 7, wherein said first fluid is a gel and said second fluid is air.

11. A device according to claim 6, wherein said at least one energy source includes a microwave antenna.

12. A device according to claim 11, wherein said first fluid is deionized water and said second fluid is a saline solution.

13. A device according to claim wherein said first fluid is air and said second fluid is a saline solution.

14. A device according to claim 11, wherein each of said first and second fluids is a saline solution.

15. A device according to claim 6, wherein said at least one energy source includes a resistive heating oil.

16. A device according to claim 15, wherein said first fluid is water and said second fluid is air.

17. A device according to claim 15, wherein said first fluid is water and said second fluid is water.

18. A device according to claim 6, wherein said at least one energy source includes an RF energy element and a return electrode that is positioned within any of said chambers containing said at least one energy source.

19. A device according to claim 18, wherein said first fluid is a saline solution and said second fluid is air.

20. A device according to claim 18, wherein said RF energy element includes alternating active and return electrodes, whereby said return electrode is formed integrally with said RF energy element.

21. A device according to claim 2, wherein said inflatable member includes a central axial lumen said energy source being located within said lumen, and said chambers extending radially outwardly from said lumen.

22. A method for selectively treating intraluminal tissue, comprising the steps of providing a inflatable member having interior which is divided into a plurality of internal chambers arranged in a circular array, each of said chambers defining a heating zone; positioning at least one energy source in said interior of said inflatable member inserting said inflatable member into the luminal structure of a patient adjacent to selected intraluminal tissue;

inflating said inflatable member and actuating said at least one energy source to thereby selectively activate one or more of said heating zones of said inflatable member such that heat is directionally delivered to said selected intraluminal tissue over a selected radially extending area.

* * * * *

UNITED STATES PATENT AND TRADEMARK OFFICE
CERTIFICATE OF CORRECTION

PATENT NO. : 6,953,469 B2  
APPLICATION NO. : 09/942412  
DATED : October 11, 2005  
INVENTOR(S) : Thomas P. Ryan It is certified that error appears in the above-identified patent and that said Letters Patent is hereby corrected as shown below:

Col. 8, cl. 1, line 54, after "zones" insert --to--  
    cl. 4, line 65, after "device" change "a cording" to --according--;  
        after "comprising" change "en" to --an--

Col. 9, cl. 13, line 22 after "claim" insert --11--  
    cl. 15, line 27, change "oil" to --coil--

Col. 10, cl. 22, line 16, after "providing" change "a" to --an--

Signed and Sealed this

Twenty-ninth Day of May, 2007

JON W. DUDAS  
*Director of the United States Patent and Trademark Office*